United States Patent [19]
Vinski et al.

[11] Patent Number: 6,120,753
[45] Date of Patent: Sep. 19, 2000

[54] CONDITIONING COSMETIC CLEANSER COMPOSITIONS

[75] Inventors: Paul Vinski, Danbury; Craig Stephen Slavtcheff, Guilford; Alexander Paul Znaiden, Trumbull, all of Conn.

[73] Assignee: Chesebrough-Pond's USA Co., division of Conopco, Inc., Greenwich, Conn.

[21] Appl. No.: 09/093,804

[22] Filed: Jun. 9, 1998

[51] Int. Cl.$^7$ .............................. A61K 7/00; A61K 7/06; A61K 7/045; A61K 31/695
[52] U.S. Cl. .................. 424/47; 424/70.1; 424/70.11; 424/70.12; 424/78.02; 514/63
[58] Field of Search ................... 424/70.1, 70.11, 424/70.12, 47, 401, 78.02; 514/63; 510/130, 135

[56] References Cited

U.S. PATENT DOCUMENTS

| | | |
|---|---|---|
| 5,120,812 | 6/1992 | O'Lenick, Jr. et al. . |
| 5,439,682 | 8/1995 | Wivell et al. . |
| 5,556,616 | 9/1996 | Janchitraponvej et al. . |
| 5,599,549 | 2/1997 | Wivell et al. . |
| 5,707,612 | 1/1998 | Zofchak et al. . |
| 5,919,441 | 7/1999 | Mendolia et al. . |

FOREIGN PATENT DOCUMENTS

| | | |
|---|---|---|
| 0 751 162 | 6/1995 | European Pat. Off. . |
| 1-211516 | 8/1989 | Japan . |
| 2 311 073 | 9/1997 | United Kingdom . |

OTHER PUBLICATIONS

International Search Report.

*Primary Examiner*—Thurman K. Page
*Assistant Examiner*—Brian K. Seidleck
*Attorney, Agent, or Firm*—Milton L. Honig

[57] ABSTRACT

An aqueous cleansing composition cleanser with moisturizing properties is disclosed including an anionic surfactant, a urethane siloxane copolymer and a nonionic water insoluble emollient.

5 Claims, No Drawings

CONDITIONING COSMETIC CLEANSER COMPOSITIONS

BACKGROUND OF THE INVENTION

1. Field of the Invention

The invention concerns a skin cleansing composition with skin and scalp moisturizing properties.

2. The Related Art

Many common anionic surfactants such as lauryl ether sulfates found in personal cleansing products can be harmful to skin or scalp. These surfactants can penetrate the stratum corneum and remove lipids. Destruction of the stratum corneum through delipidization leads to dry rough skin.

Cleansing products should not only contain mild surfactants, they should provide protective ingredients such as moisturizers. Two-in-one body products have come onto the market to address these needs. Yet often a problem with these formulations is that moisturization additives can have an adverse effect upon foam properties.

U.S. Pat. No. 5,599,549 (Wivell et al.) discloses a combined personal cleansing and moisturizing composition delivered via a non-aerosol mechanical pump. These compositions contain at least one anionic surfactant, a dispersed insoluble oil phase, at least one additional surfactant and water.

U.S. Pat. No. 5,707,612 (Zofchak et al.) reports copolymers of castor oil with isophorone diisocyanate urethanes in skin and personal care products. These copolymers were found particularly effective in lipstick formulations. They improve pigment dispersibility, increase lip fill, heighten sheen and gloss, enhance glide, improve adhesion and increase moisturization of the lipsticks in contrast to straight castor oil itself.

While it is evident that advances have been made in cleansing technology, there is still room for improvement. Specifically it is desired to obtain thicker, more robust, richer foams which before collapsing are long-lived. Improvements in surfactant mildness and moisturization are further goals.

Accordingly, it is an object of the present invention to provide a cleansing composition with improved moisturization and skin after feel benefits.

Another object of the present invention is to provide a cleansing composition which achieves thicker, richer and longer standing foam.

Still another object of the present invention is to provide a cleansing composition with moisturization benefits which can be dispensed from pump devices, especially from aerosol pressurized containers.

These and other objects of the present invention will become more readily apparent from the summary and detailed description which follow.

SUMMARY OF THE INVENTION

An aqueous cleansing composition with moisturization benefits is provided including:

(i) from about 0.1 to about 40% by weight of an anionic surfactant;

(ii) from about 0.1 to about 20% by weight of a urethane siloxane copolymer; and (iii) from about 0.1 to about 30% by weight of a nonionic water-insoluble emollient.

DETAILED DESCRIPTION OF THE INVENTION

Now it has been discovered that a cleansing composition with excellent foaming and moisturization can be achieved through an aqueous composition containing a urethane siloxane copolymer, an anionic surfactant and a nonionic water-insoluble emollient.

Thus, essential for the present invention is a urethane siloxane copolymer which is either water soluble or, when insoluble is at least water dispersible. Most preferable is the water soluble variety. Copolymers of the present invention may be characterized by the following formula:

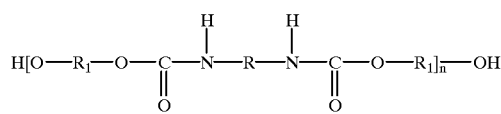

wherein R is a $C_1$–$C_{50}$, preferably $C_6$–$C_{25}$ alkylene, cycloalkylene or arylene radical, $R_1$ is a polysiloxane or alkoxylated polysiloxane radical; and n ranges from 1 to 1,000, preferably from 2 to 100 and optimally from 3 to 50.

Copolymers of the above structure usually are prepared by the reaction of a diol with an organic diisocyanate. Suitable diols include dimethiconol and polydimethyl siloxane. Diisocyanates which are most commercially available are isophorone diisocyanate (IPDI), methylene diisocyanate (MDI) and toluene diisocyanate (TDI). The copolymers are commercially available from Alzo Inc., Matawan, N.J. under the product description PPI-SI for Dimethiconol/IPDI Copolymer;

PPI-SI-50 for Dimethiconol/Cyclomethicone/IPDI Copolymer; PPI-SI-WI for Polydimethyl Siloxane-PPG Ether/IPDI Copolymer; and PPI-SI-WS for Polydimethyl Siloxane-PEG Ether/IPDI Copolymer. The latter material is preferred and known by its chemical name as Polydimethylsiloxane-Polyoxyalkyleneoxide Polymer with 3-Isocyanatomethyl-3,5,5-trimethylcyclohexyl Isocyanate.

Amounts of the urethane siloxane copolymer may range from about 0.1 to about 20%, preferably from about 0.5 to about 10%, optimally from about 1 to about 3% by weight.

A second essential element of compositions according to the present invention is that of an anionic surfactant. Illustrative but not limiting examples include the following classes:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3$—$M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®.

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3-M+)CO_2R^2$ where $R^1$ is straight or branched alkyl from about $C_8$ to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Mono- and dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

Co-surfactants may also be present to aid in the foaming, detergency and mildness properties. Nonionic and amphoteric actives are the preferred co-surfactants. Suitable nonionic surfactants include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di- fatty acid esters of ethylene glycol such as ethylene glycol distearate; fatty acid monoglycerides; sorbitan mono- and di- $C_8$–$C_{20}$ fatty acids; and polyoxyethylene sorbitan available as Polysorbate 80 and Tween 80® as well as combinations of any of the above surfactants.

Other useful nonionic surfactants include alkyl polyglycosides (APGs), saccharide fatty amides (e.g. methyl gluconamides) as well as long chain tertiary amine oxides. Examples of the latter category are: dimethyldodecylamine oxide, oleyldi(2-hydroxyethyl)amine oxide, dimethyloctylamine oxide, dimethyldecylamine oxide, dimethyltetradecylamine oxide, di(2-hydroxyethyl)tetradecylamine oxide, 3-didodecyloxy-2-hydroxypropyldi(3-hydroxypropyl) amine oxide, and dimethylhexadecylamine oxide.

Amounts of the nonionic surfactant may range from about 0.1 to about 40% preferably from about 0.5 to about 15%, optimally from about 1 to about 5% by weight of the total composition.

Amphoteric surfactants such as betaines may also be employed as co-actives along with the anionic surfactants. Suitable betaines may have the general formula $RN^+(R^1)_2R^2COO^-$ wherein R is a hydrophobic moiety selected from the group consisting of alkyl groups containing from 10 to 22 carbon atoms, preferably from 12 to 18 carbon atoms; alkyl aryl and aryl alkyl groups containing 10 to 22 carbon atoms with a benzene ring being treated as equivalent to about 2 carbon atoms, and similar structures interrupted by amido or ether linkages; each $R^1$ is an alkyl group containing from 1 to 3 carbon atoms; and $R^2$ is an alkylene group containing from 1 to about 6 carbon atoms. Sulfobetaines such as cocoamidopropyl hydroxysultaine are also suitable.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate. Most preferred is cocoamidopropyl betaine available as Tegobetaine F® sold by Th. Goldschmidt AG of Germany. Amounts of the betaine may range from about 0.05 to about 15%, preferably from about 0.5 to about 10%, optimally from about 2 to about 8% by weight of the total composition.

Another essential element of the present invention is that of a nonionic water insoluble emollient. The emollient may be selected from hydrocarbons, silicones and synthetic or vegetable esters. Amounts of the emollients may range anywhere from about 0.1 to about 30%, preferably between about 0.5 and about 10% by weight of the total composition.

Hydrocarbons suitable for the present invention include isoparaffins, mineral oil, petrolatum and hydrocarbon waxes such as polyethylenes.

Silicones may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicone atoms.

Nonvolatile silicones useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among suitable ester emollients are:

(1) Alkenyl or alkyl esters of fatty acids having 10 to 20 carbon atoms. Examples thereof include isopropyl palmitate, isononyl isononoate, oleyl myristate, oleyl stearate, cetearyl stearate and oleyl oleate.

(2) Ether-esters such as fatty acid esters of ethoxylated fatty alcohols.

(3) Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Steroids esters, of which soya sterol and cholesterol fatty acid esters are examples thereof.

Most preferred vegetable ester emollients are sunflower seed oil, soy sterol esters, borage seed oil, maleated soybean oil and mixtures thereof.

Fatty acids having from 10 to 30 carbon atoms may be included in the compositions of this invention. Illustrative of this category are pelargonic, lauric, myristic, palmitic, stearic, isostearic, hydroxystearic, oleic, linoleic, ricinoleic, arachidic, behenic and erucic acids. Amounts may range from 0.1 to 25% by weight.

Preservatives can desirably be incorporated into the compositions of this invention to protect against the growth of potentially harmful microorganisms. Suitable traditional preservatives are EDTA salts and alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from 0.01% to 2% by weight of the composition.

Minor adjunct ingredients may be present in the compositions. Among them may be the water-insoluble vitamins such as Vitamin A Palmitate, Vitamin E Acetate and DL-panthenol. Colorants, fragrances and opacifiers are further possible additives. Each of these substances may range from about 0.05 to about 5%, preferably between about 0.1 and about 3% by weight of the composition.

Cationic conditioning agents in monomeric and polymeric type are also useful for purposes of this invention. Examples of the polymeric type include: cationic cellulose derivatives, cationic starches, copolymers of a diallyl quaternary ammonium salt and an acrylamide, quaternized vinylpyrrolidone vinylimidazole polymers, polyglycol amine condensates, quaternized collagen polypeptide, polyethylene imine, cationized silicone polymer (e.g. Amodimethicone), cationic silicone polymers provided in a mixture with other components under the trademark Dow Corning 929 (cationized emulsion), copolymers of adipic acid and dimethylamino-hydroxypropyl diethylenetriamine, cationic chitin derivatives, cationized guar gum (e.g. Jaguar® C-B-S, Jaguar® C-17, Jaguar® C-16, etc. manufactured by the Celanese Company), quaternary ammonium salt polymers (e.g. Mirapol® A-15, Mirapol® AD-1, Mirapol® AZ-1, etc., manufactured by the Miranol Division of the Rhone Poulenc Company). Most preferred is polyquaternium-11 available as Luviquat® PQ 11 sold by the BASF Corporation.

Examples of monomeric cationic conditioning agents are salts of the general structure:

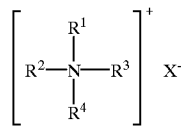

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carton atoms, or aromatic, aryl or alkaryl groups having from 12 to 22 carbon atoms; and $X^-$ is an anion selected from chloride, bromide, iodide, acetate, nitrate, sulfate, methyl sulfate, ethyl sulfate, tosylate, lactate, citrate, glycolate, and mixtures thereof. Additionally, the alkyl groups can also contain ether linkages or amino group substituents (e.g., the alkyl groups can contain polyethylene glycol and polypropylene glycol moieties).

Amino silicone quats may similarly be employed. Most preferred is Silquat AD designated by the CTFA as Silicone Quaternium 8, available from Siltech Inc.

Amounts of each cationic conditioning agent may range from about 0.05 to about 5%, preferably from about 0.1 to about 3%, optimally from about 0.3 to about 2.5% by weight.

Compositions of this invention when dispensed through certain types of pumps may require to be of relatively low viscosity to ensure pumpability. Viscosity may range from 0.1 to 80 centipoise, preferably from 1 to 50 centipoise, optimally from 3 to 20 centipoise at 25° C.

Water-soluble moisturizing ingredients may also be included in compositions of the present invention. Water soluble moisturizers such as polyhydric alcohol-type humectants are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from about 0.5 to about 30%, preferably between about 1 and about 15% by weight of the composition.

Compositions of the present invention are water and oil emulsions. They may be oil-in-water or water-in-oil, although the former is preferred. Relative weight ratios of water to oil phases of the emulsion may range from about 1,000:1 to about 1:10, preferably from about 100:1 to about 1:5, optimally from about 10:1 to about 1:2 by weight. Amounts of water may range from about 0.01 to about 99%, preferably from about 10 to about 90%, optimally from about 40 to about 80% by weight.

Compositions of this invention may be dispensed through a pump device. The device may either be a non-aerosol or aerosol variety. The former operates through use of pumped air pressure while the latter includes a propellant such as a hydrocarbon (e.g. propane, n-butane, isobutane, isopropane, pentane and combinations thereof), halocarbons (e.g. trifluorochloromethane), dimethyl ether and combinations thereof. Preferred propellants are combinations of hydrocarbon (such as A31) and dimethyl ether (DME) in weight ratios ranging from about 10:1 to 1:10 but preferably from about 2:1 to about 1:2 by weight. Relative ratios of compositions according to the present invention (i.e. concentrate) to propellant may vary from about 50:1 to about 5:1, preferably from about 15:1 to about 10:1 by weight. Amounts of propellant may range from about 1 to about 15%, preferably from about 3 to about 6% by weight.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight of the total composition unless otherwise indicated.

EXAMPLES

The following examples include representative cleansing compositions according to the present invention. The formulas of these compositions (i.e. concentrates) are reported in Table I. They were tested for foam quality in combination with a propellant (92% concentrate/8% propellant) (A31/DME).

TABLE I

FORMULATIONS

CONCENTRATE (WEIGHT %)

| INGREDIENT NAME | A | B | C | D | E | F | G | H | I | J | K | L | M |
|---|---|---|---|---|---|---|---|---|---|---|---|---|---|
| Phase A | | | | | | | | | | | | | |
| Sunflower Seed Oil | 0.00 | 0.00 | 0.00 | 0.00 | 0.00 | 20.00 | 20.00 | 20.00 | 20.00 | 20.00 | 20.00 | 20.00 | 20.00 |
| Maleated Soybean Oil | 0.00 | 0.00 | 0.00 | 0.00 | 0.00 | 5.00 | 5.00 | 5.00 | 5.00 | 5.00 | 5.00 | 5.00 | 5.00 |
| Polyderm PPI-Si-WS (Silicone Urethane) | 0.00 | 0.00 | 0.00 | 0.00 | 0.00 | 0.00 | 0.00 | 0.00 | 0.00 | 1.00 | 1.00 | 0.00 | 1.00 |
| Dimethicone | 0.00 | 0.00 | 0.00 | 0.00 | 0.00 | 0.00 | 0.00 | 0.00 | 0.00 | 0.00 | 0.00 | 1.00 | 0.00 |
| Phase B | | | | | | | | | | | | | |
| Isolan PD ® (Nonionic Emulsifier, ex. Goldschmidt Inc.) | 0.00 | 0.00 | 0.00 | 0.00 | 0.00 | 0.00 | 0.00 | 1.00 | 1.00 | 1.00 | 1.00 | 1.00 | 1.00 |
| Phase C | | | | | | | | | | | | | |
| Bioterge AS 40 (Sodium C14–16 Olefin Sulfonate) | 0.00 | 60.00 | 0.00 | 0.00 | 15.00 | 0.00 | 15.00 | 15.00 | 15.00 | 15.00 | 15.00 | 15.00 | 15.00 |
| Sodium Lauryl Ether Sulfate/Lauryl Sulphate (25% Active) | 60.00 | 0.00 | 0.00 | 0.00 | 15.00 | 0.00 | 15.00 | 15.00 | 15.00 | 15.00 | 15.00 | 15.00 | 15.00 |
| Proteol OAT (Na Lauroyl Oat Aminoacid) | 0.00 | 0.00 | 0.00 | 60.00 | 15.00 | 0.00 | 15.00 | 15.00 | 15.00 | 15.00 | 15.00 | 15.00 | 15.00 |
| Tegobetaine ® F (30%) | 0.00 | 0.00 | 60.00 | 0.00 | 15.00 | 0.00 | 15.00 | 15.00 | 15.00 | 15.00 | 15.00 | 15.00 | 15.00 |
| Phase D | | | | | | | | | | | | | |
| DC 1784 (Silicone Emulsion 50%) | 0.00 | 0.00 | 0.00 | 0.00 | 0.00 | 0.00 | 0.00 | 0.00 | 0.00 | 0.00 | 5.00 | 5.00 | 5.00 |
| Phase E | | | | | | | | | | | | | |
| Deionized Water | 40.00 | 40.00 | 40.00 | 40.00 | 40.00 | 75.00 | 15.00 | 14.00 | 13.00 | 12.00 | 7.00 | 7.00 | 7.00 |
| Luviquat ® PQ11 (Polyquaternium-11) (20%) | 0.00 | 0.00 | 0.00 | 0.00 | 0.00 | 0.00 | 0.00 | 0.00 | 1.00 | 1.00 | 1.00 | 1.00 | 0.00 |
| Cetrimonium Chloride ($C_{16}$ Ammonium Salt) | 0.00 | 0.00 | 0.00 | 0.00 | 0.00 | 0.00 | 0.00 | 0.00 | 0.00 | 0.00 | 0.00 | 0.00 | 1.00 |
| | 100.00 | 100.00 | 100.00 | 100.00 | 100.00 | 100.00 | 100.00 | 100.00 | 100.00 | 100.00 | 100.00 | 100.00 | 100.00 |

The concentrate formulations were prepared by charging water to form Phase A in a main vessel. Phase A was stirred and heated at 50° C. Phase B and C were then added and allowed to slowly dissolve. The remaining phases were separately prepared, each added in the listed order and allowed to dissolve. Heating and stirring were continued until a uniform mixture was obtained. Concentrate was then filled into steel pressure cans fitted with spray nozzles. Propellant was then charged into the filled cans. Results of dispensing tests are reported in Table II.

TABLE II

Performance
COMMENTS

A Considerable lather; poor dispensibility; poor afterfeel.
B Dispensibility OK; lather quality poor; afterfeel very stripping.
C Dispensibility OK; lather quality very poor; foam very loose; afterfeel OK.
D Dispensibility OK; lather quality poor; low foam volume; afterfeel very nice.
E Dispensibility lather quality good; afterfeel better but not good.
F Dispensibility poor; no foam generation; afterfeel oily; evenly separates.

TABLE II-continued

Performance
COMMENTS

G Dispensibility good; lather quality good; nice creamy foam but afterfeel is lost, Formulation - begins to separate.
H Dispensibility good; lather quality good; nice creamy foam & afterfeel is better, Formulation - emulsion stability improved.
I Dispensibility good; lather quality good; nice creamy foam, afterfeel is better - more moisturized.
J Dispensibility good; lather quality good; nice creamy foam afterfeel excellent - more substantive, moisturized (much better than concentrate I).
K Dispensibility excellent; dispenses nice creamy foam - lather more lubricious; afterfeel excellent - more substantive, moisturized.
L Replaced Silicone Urethane w/Dimethicone @ 1%; Dispensibility worsens; depresses foam - lather feels heavy.
M Replace QP11 w/Cetrimonium Chloride @ 1%; Incompatibility - cationic complexes w/anionic surfactant.

The term "comprising" is meant not to be limiting to any subsequently stated elements but rather to encompass non-specified elements of major or minor functional importance. In other words, the listed steps, elements or options need not be exhaustive.

The foregoing description and examples illustrate selected embodiments of the present invention. In light thereof variations and modifications will be suggested to one skilled in the art, all of which are within the spirit and purview of this invention.

What is claimed is:

1. An aqueous cleansing composition comprising:
   (i) from about 0.1 to about 40% by weight of an anionic surfactant;
   (ii) from about 0.1 to about 20% by weight of a urethane siloxane copolymer having the structure:

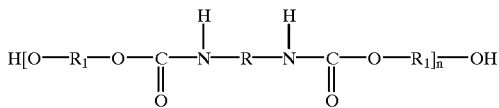

wherein R is a $C_1$–$C_{50}$ material selected from the group consisting essentially of alkylene, cycloalkylene and arylene radicals; $R_1$ is a polysiloxane or alkoxylated polysiloxane radical; and n ranges from 1 to 1,000; and
   (iii) from about 0.1 to about 30% by weight of a nonionic water-insoluble emollient selected from the group consisting of sunflower seed oil, soy sterol esters, borage seed oil, maleated soybean oil, mineral oil, isoparaffin, petrolatum, silicon emulsion and mixtures thereof.

2. The composition according to claim 1 wherein the anionic surfactant is selected from the group consisting of sodium lauryl ether sulfate, sodium $C_{14}$–$C_{16}$ olefin sulfonate and mixtures thereof.

3. The composition according to claim 1 further comprising at least one cationic conditioning agent present in a range from about 0.05 to about 5% by weight.

4. The composition according to claim 3 wherein the cationic conditioning agent is polyquaternium-11.

5. The composition according to claim 1 further comprising a propellant present in an amount from about 1 to about 15% by weight of the total composition.

* * * * *